(12) United States Patent
Mo et al.

(10) Patent No.: US 10,401,286 B1
(45) Date of Patent: Sep. 3, 2019

(54) REFLECTIVITY ANALYSIS TO DETERMINE MATERIAL ON A SURFACE

(71) Applicant: Intel Corporation, Santa Clara, CA (US)

(72) Inventors: Jianyong Mo, Chandler, AZ (US); Darren Vance, Gilbert, AZ (US); Di Xu, Chandler, AZ (US); Liang Zhang, Chandler, AZ (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 15/934,722

(22) Filed: Mar. 23, 2018

(51) Int. Cl.
| | | |
|---|---|---|
| G01N 21/55 | (2014.01) |
| G06T 7/00 | (2017.01) |
| G06T 1/00 | (2006.01) |
| G01N 21/17 | (2006.01) |

(52) U.S. Cl.
CPC ........... G01N 21/55 (2013.01); G06T 1/0007 (2013.01); G06T 7/0004 (2013.01); *G01N 2021/1742* (2013.01)

(58) Field of Classification Search
CPC ............ G01N 21/55; G01N 2021/1742; G06T 1/0007; G06T 7/0004
USPC ........................................................ 356/612
See application file for complete search history.

(56) References Cited

U.S. PATENT DOCUMENTS

| | | | | |
|---|---|---|---|---|
| 5,835,220 A | * | 11/1998 | Kazama | G01J 4/04 356/369 |
| 6,512,578 B1 | * | 1/2003 | Komatsu | G01N 21/9501 356/237.5 |
| 6,542,248 B1 | * | 4/2003 | Schwarz | G01B 11/303 356/446 |
| 7,385,710 B1 | * | 6/2008 | Sturgill | G01B 11/06 356/632 |
| 8,422,009 B2 | * | 4/2013 | Yamashita | G01N 21/94 356/237.2 |
| 2008/0013075 A1 | * | 1/2008 | Schwarz | G01N 21/4738 356/73 |
| 2008/0246966 A1 | * | 10/2008 | Oomori | G01N 21/956 356/364 |
| 2009/0219499 A1 | * | 9/2009 | Yamaguchi | G01B 11/0608 355/67 |
| 2012/0134693 A1 | * | 5/2012 | Hoshi | G03G 15/5029 399/45 |

* cited by examiner

*Primary Examiner* — Roy M Punnoose
(74) *Attorney, Agent, or Firm* — Schwabe, Williamson & Wyatt, P.C.

(57) ABSTRACT

Embodiments herein relate to identifying whether a threshold amount of material is on a surface. In particular, an apparatus may have an inspection module to receive an image of a surface captured by a camera, where the surface is illuminated by a light source positioned at an angle to the surface. The apparatus may then analyze the received image to identify a measurement of light intensity of one or more portions of the surface; and determine, based on the analysis, whether each of the one or more portions of the surface includes a threshold amount of a material on the surface.

25 Claims, 5 Drawing Sheets

REFLECTIVITY ANALYSIS TO DETERMINE MATERIAL ON A SURFACE

FIELD

Embodiments of the present disclosure generally relate to the field of die manufacturing, and in particular identifying whether a surface is coated with a material.

BACKGROUND

The background description provided herein is for the purpose of generally presenting the context of the disclosure. Unless otherwise indicated herein, the materials described in this section are not prior art to the claims in this application and are not admitted to be prior art by inclusion in this section.

Process material, such as solder flux, may be applied to a surface during a manufacture process. For example, in microelectronics manufacture, the material may be placed with a desired coverage profile over a designated region on the surface.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example, and not by way of limitation, in the figures of the accompanying drawings.

DETAILED DESCRIPTION

Figure 1:
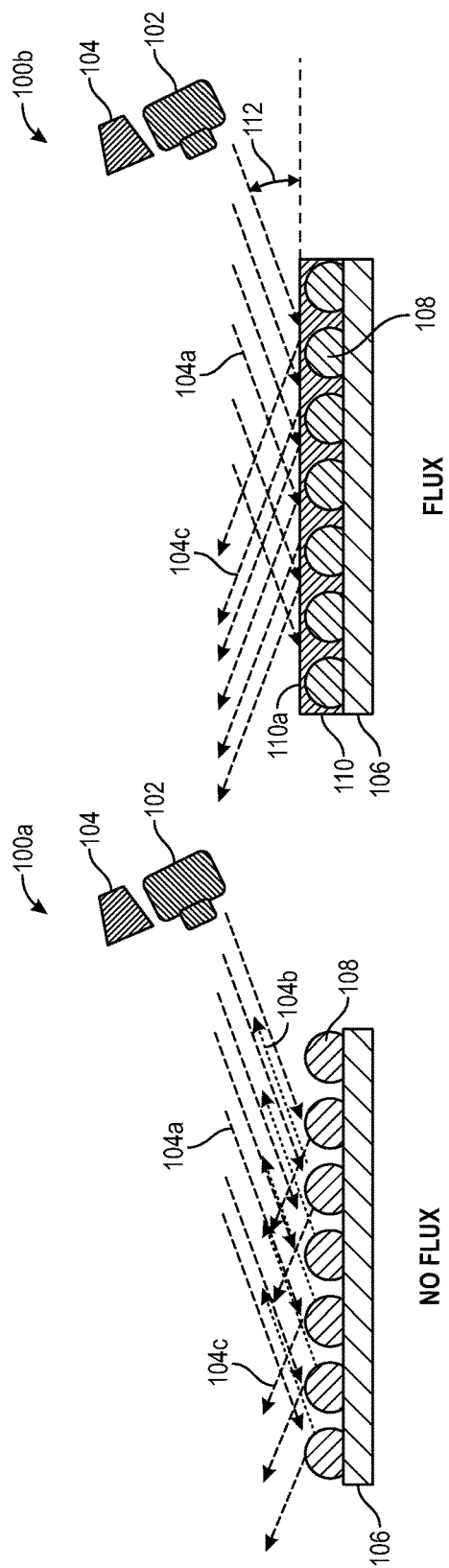
FIG. 1 illustrates example systems with a surface, camera, and light source to detect whether a material is applied to a surface, in accordance with various embodiments.

Embodiments of the present disclosure generally relate to apparatuses, processes, or systems to detect materials placed on a surface based upon angle-dependent reflectivity of the material on the surface. In particular, an apparatus may receive an image of a surface captured by a camera, where the surface may be illuminated by a light source positioned at an angle to the surface. The apparatus may analyze the received image to identify a measurement of reflectivity of one or more portions of the surface. The apparatus may then determine, based on the analysis, whether each of the one or more portions of the surface includes a threshold amount of a material on the surface.

Light, particularly at certain angles, may reflect differently off a smooth surface in comparison to a rough surface. A camera may be pointed at a surface, with a light source proximate to the camera illuminating the surface. The intensity (e.g., lightness or darkness) of an image captured by a camera may appear different based on the smoothness or roughness of the surface. In particular, the image intensity of the smooth surface may appear lower (e.g., the image may be darker) and the image intensity of the rough surface may appear higher (e.g., the image may be lighter). This may result from light rays at angles of low incidence with respect to a smooth surface reflecting off the smooth surface directionally at a similar incident angle and continuing generally in the same direction away from the camera. In contrast, light rays at angles of low incidence with respect to a rough surface reflect omnidirectionally off the rough surface with some light rays reflecting off bumps in the surface back toward the camera. This may result in a higher intensity image. Material, such as a flux coating, applied to a rough surface may smooth the surface, resulting in more directional reflection and less omnidirectional reflection of rays back toward the camera, resulting in a lower intensity image. In this way, the intensity of the image may indicate the degree to which an irregular surface may be smoothed by a layer of surface material.

Such behavior of light reflectivity may apply whether the applied material is a solid or a liquid, whether the material is transparent or opaque, or whether the material is watery, gelatinous or viscous. This difference in how light reflects off the surface, omnidirectional versus directional, may be used to determine the presence of and coverage of the applied process material on the surface.

In embodiments, a detection system may include a light and a camera that are connected to an inspection module. The system may be integrated into manufacturing process assembly systems and tools. The camera may be an autofocus camera, and may have a varying depth of field. The light source may be placed at a glancing angle to the target surface. In embodiments, the light source and the camera may be at substantially the same location.

For example, a rough surface such as a substrate having a C4 bump area, when illuminated, may produce an omnidirectional reflection of light, which may be captured by the camera as a higher intensity (lighter) image. A flux fluid covering the C4 bump area on the substrate may reflect the majority of the light away from the camera and thus may result in a lower intensity (darker) image captured by the camera, based upon the surface reflectivity change due to the presence of the flux fluid. In the case where the fluid coverage is non-uniform on the bump area, areas of higher light intensity (lighter) may indicate little or no fluid coverage, and areas of lower light intensity (darker) may indicate adequate fluid coverage.

Examples of embodiments directed to image analysis of substrate surfaces may result in a faster and easier detection of flux coverage on substrates. As a result, this information may be used to optimize a flux dispense process, or may be used to quickly identify and remove substrates from an assembly process that do not meet quality standards. These techniques may also be used to determine the relative smoothness or roughness of any surface.

In embodiments, these techniques may be used to identify a smooth surface that may have materials applied to the surface that may make the surface rough. For example, for detecting sand or other material that may be on a glass surface. In these embodiments, a lighter intensity image of a surface may be captured to identify a rough area that may indicate further action is to be taken with respect to the surface.

In the following detailed description, reference is made to the accompanying drawings which form a part hereof, wherein like numerals designate like parts throughout, and in which is shown by way of illustration embodiments in which the subject matter of the present disclosure may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The description may use perspective-based descriptions such as top/bottom, in/out, over/under, and the like. Such descriptions are merely used to facilitate the discussion and are not intended to restrict the application of embodiments described herein to any particular orientation.

The description may use the phrases "in an embodiment," or "in embodiments," which may each refer to one or more of the same or different embodiments. Furthermore, the terms "comprising," "including," "having," and the like, as used with respect to embodiments of the present disclosure, are synonymous.

The term "coupled with," along with its derivatives, may be used herein. "Coupled" may mean one or more of the following. "Coupled" may mean that two or more elements are in direct physical or electrical contact. However, "coupled" may also mean that two or more elements indirectly contact each other, but yet still cooperate or interact with each other, and may mean that one or more other elements are coupled or connected between the elements that are said to be coupled with each other. The term "directly coupled" may mean that two or more elements are in direct contact.

Various operations may be described as multiple discrete operations in turn, in a manner that is most helpful in understanding the claimed subject matter. However, the order of description should not be construed as to imply that these operations are necessarily order dependent.

As used herein, the term "module" may refer to, be part of, or include an application specific integrated circuit (ASIC), an electronic circuit, a processor (shared, dedicated, or group) and/or memory (shared, dedicated, or group) that execute one or more software or firmware programs, a combinational logic circuit, and/or other suitable components that provide the described functionality.

FIG. 1 illustrates example systems with a surface, camera, and light source to detect whether a material is applied to a surface, in accordance with various embodiments. Diagrams 100a and 100b show two different examples of a camera 102 and a light source 104 used to capture images.

In diagram 100a, the surface 106 may include surface bumps 108 that may texture the surface 106. In embodiments, light rays 104a from light source 104, after striking surface 106 with surface bumps 108, may result in light rays 104b bouncing off portions of surface bumps 108 and reflecting back toward camera 102. Light rays 104b may reflect off areas of surface bumps 108 that may be substantially orthogonal to the direction of light rays 104a. The light rays 104b may cause images captured by the camera 102 (described further in FIG. 2) of the surface 106 to have a higher intensity, or to appear lighter. Other scattered light rays 104c may bounce off surface bumps 108 away from the camera 102. As a result, the more textured the surface 106 with surface bumps 108, the greater the omnidirectional reflection of light rays 104b, 104c, and the higher intensity (lighter) the image recorded by the camera 102 of the surface 106.

In contrast, in diagram 100b, a material 110 covers the surface 106, including any surface bumps 108. In embodiments, the material 110 may be a flux, and the surface 106 may be a substrate. In embodiments, the material 110 may form a planar surface 110a that may be smooth or have a smoothing effect. In embodiments, the planar surface 110a may be a liquid-air interface. In embodiments, the material 110 may be transparent or have varying degrees of opacity. In embodiments, the material 110 may be a solid or liquid with varying degrees of viscosity. When light rays 104a strike the planar surface 110a of material 110, most light rays 104c may be directly reflected away from the camera 102 due to the planar surface 110a. As a result, an image recorded by the camera 102 of the surface 106 coated with the material 110 may have less intensity and appear darker.

In diagram 100b, varying the incident angle 112 may vary the amount of the directly reflected light rays 104c resulting from hitting the surface 110a. In embodiments, as the incident angle 112 decreases, a majority of the light rays 104a hitting the surface 110a may result in directly reflected light rays 104c. As the incident angle 112 increases, more light rays 104a may penetrate the planar surface 110a, and reflect off of surface bumps 108, resulting in omnidirectional reflection and an increase in reflected light rays 104b (as shown in diagram 100a). As a result, a higher intensity (lighter) image of the surface 106 may result as the incident angle 112 increases.

In embodiments, the light source 104 may be a light bar, or some other suitable source of light. In embodiments, the light source 104 may emit collimated light, where the individual rays of light emanating from the light source 104 are substantially parallel. In embodiments, the light source 104 may emit light of any wavelength, with light in the visible spectrum or infrared spectrum preferred. The light source 104 may emit either polarized or non-polarized light. The light source 104 may operate in a strobing mode or a continuous mode.

Figure 2:
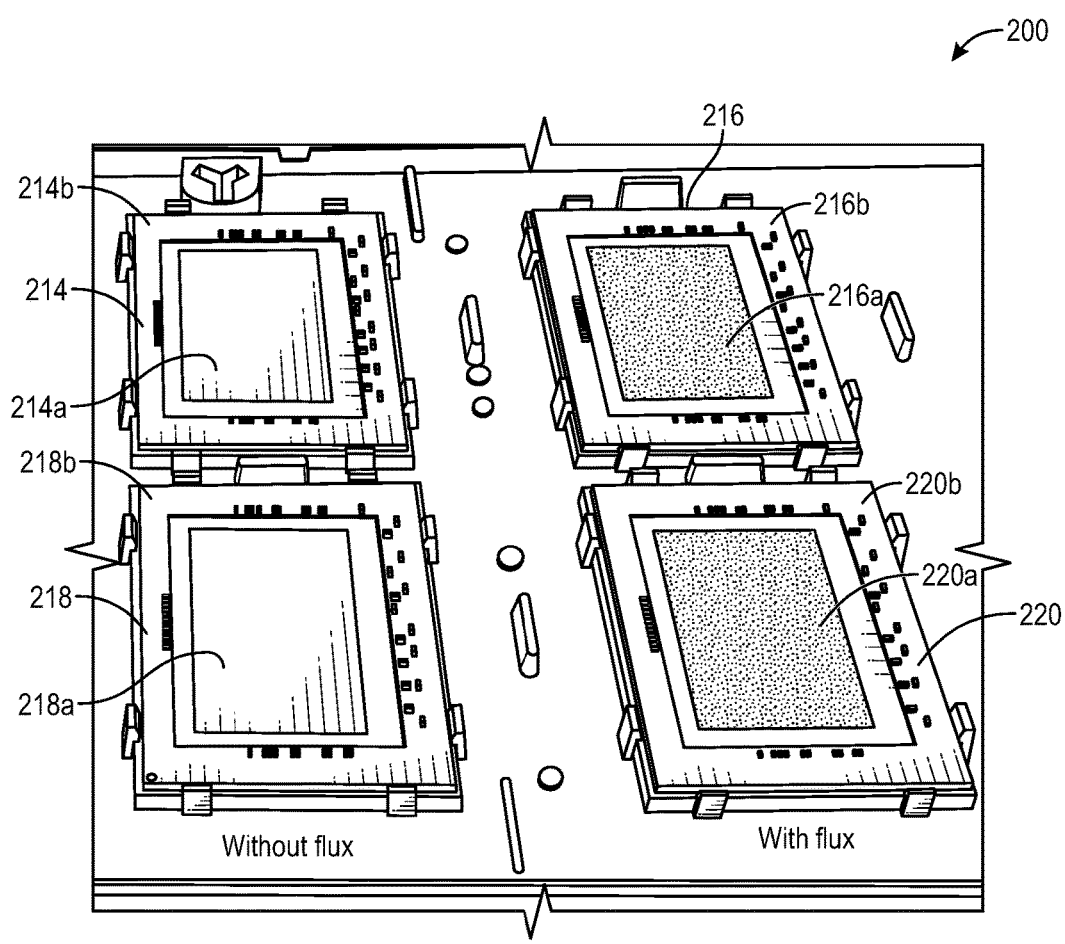
FIG. 2 illustrates an example substrate with and without a flux coating applied, in accordance with various embodiments.

FIG. 2 illustrates an example substrate with and without a flux coating applied, in accordance with various embodiments. Diagram 200 shows an image of four substrates 214, 216, 218, 220 taken with the camera that may be similar to camera 102 of FIG. 1, illuminated with a light source that may be similar to light source 104 of FIG. 1. Diagram 200 may be an image captured during the manufacturing process involving the four substrates 214, 216, 218, 220. The areas 214a and 218a showing on substrates 214, 218 respectively are areas with no flux coating. The areas 216a and 220a showing on substrates 216, 220 respectively are areas that have flux coating, such as material 110 of FIG. 1. In embodiments, the areas 214a, 218a may have a higher intensity and may appear lighter than a determined threshold intensity value. The higher image intensity may indicate an absence of flux coating due to an increased amount of scattered light reflecting back to the camera from the rough surface. In embodiments, the areas 216a, 220a may appear with lower intensity and may appear darker than the determined threshold intensity value to indicate the presence of a flux coating, due to an increased amount of directly reflected light rays 104c away from the camera.

In embodiments, a threshold intensity value may be determined by analyzing an image of a marker, such as marker 214b, 216b, 218b, 220b of substrates 214, 216, 218, 220, where the marker may be either a textured area of the substrate or a smooth area of the substrate. In embodiments, the threshold intensity value may be predetermined prior to the manufacturing process. In embodiments, the threshold intensity value may be determined based upon attributes of the light source, such as light source 104 of FIG. 1, the incident angle, such as incident angle 112 of FIG. 1, and/or the ambient light. Once the threshold intensity value is determined, areas 214*a*, 216*a*, 218*a*, 220*a* may be analyzed by comparing the intensity of a portion of the image to the threshold intensity value.

Figure 3:
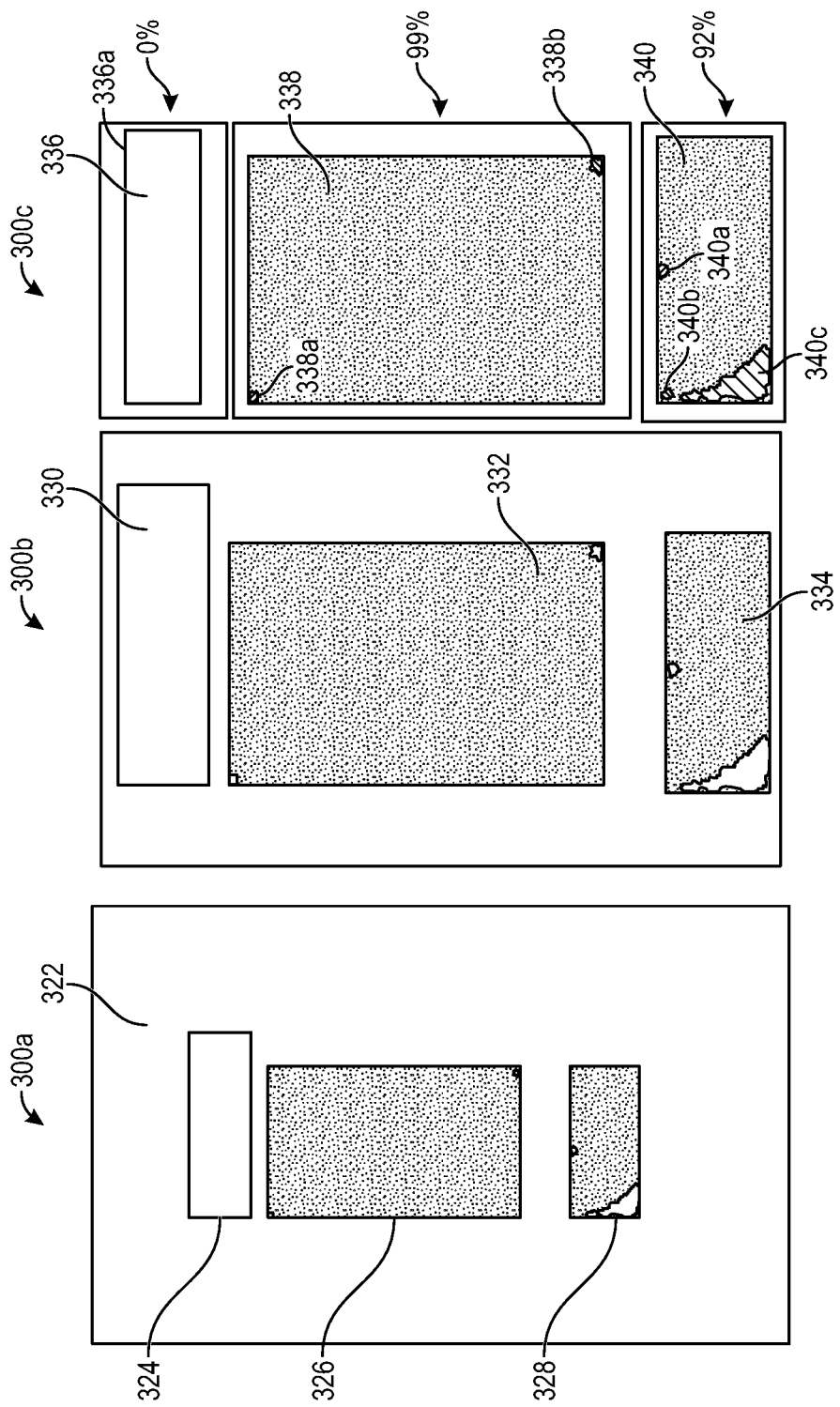
FIG. 3 illustrates an example substrate with partial flux coating, in accordance with various embodiments.

FIG. 3 illustrates an example substrate with partial flux coating, in accordance with various embodiments. Diagram 300*a* shows an image of a substrate 322 that includes a first die 324, a second die 326, and a third die 328, each having a different amount of flux applied. Diagram 300*a* may have been captured by a system similar to diagram 100*a* of FIG. 1 that includes a camera 102 and a light source 104.

In embodiments, the diagram 300*a* may have first been altered to correct image perspective distortions produced by a camera 102 placed at a low incident angle (such as incident angle 112). For example, without correction, the image of the rectangular substrate 322 may appear trapezoidal. In embodiments, the perspective correction may produce a nadir (e.g., top-down) image, such as shown in diagram 300*a*. This is described further with respect to FIG. 4.

Diagram 300*b* shows an image with the three dies 324, 326, 328 segmented out of the substrate 322 to create, respectively, three die images 330, 332, 334. This segmentation may be accomplished by using known techniques, for example, by using color difference, edge detection techniques, pre-identified image coordinates, etc. Image analysis may then be performed on the three die images 330, 332, 334.

Diagram 300*c* shows results of the image analysis performed on the three die images 330, 332, 334 to identify areas that may have insufficient flux coverage. Post analysis image 336 shows a boundary area 336*a* around the entire image 336 to indicate that the entire area had insufficient flux coverage. In this example, the analysis indicated that all areas of the image 336 were above a threshold intensity value, indicating a 0% coverage of flux. In this case, the first die represented by the image 330 may be flagged for flux reapplication or for scrapping.

Post analysis image 338 shows two boundary areas 338*a* and 338*b* that indicate areas with insufficient flux coverage. In this example, the analysis indicated that areas 338*a* and 338*b* had an intensity above a threshold intensity value, indicating a 99% coverage of flux. In this case, the second die represented by the image 332 may have an acceptable flux coverage and may proceed to the next action in the manufacturing process.

Post analysis image 340 shows three boundary areas 340*a*, 340*b*, 340*c* that indicate areas with insufficient flux coverage. In this example, the analysis indicated that areas 340*a*, 340*b*, 340*c* were above a threshold intensity level, indicating a 92% coverage of flux. In this case, the third die represented by the image 334 may be flagged for either flux reapplication or for scrapping.

Figure 4:
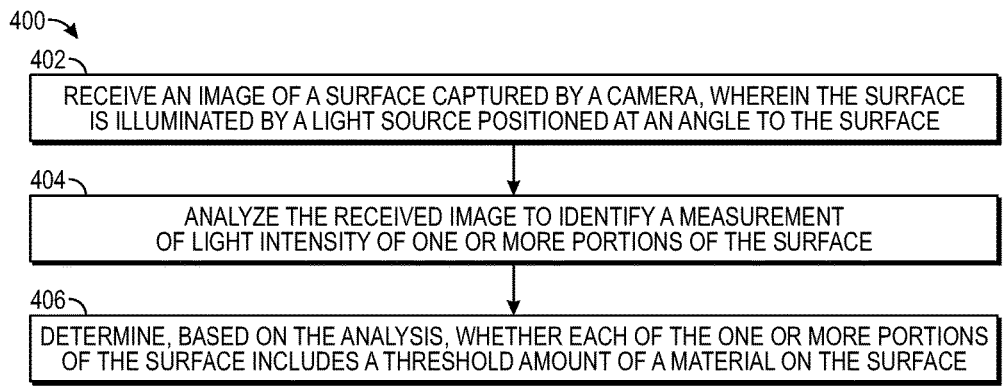
FIG. 4 illustrates an example process for detecting material applied to a surface, in accordance with embodiments.

FIG. 4 illustrates an example process for detecting material applied to a surface, in accordance with embodiments. Process 400 may be implemented using the camera 102 and light source 104 of FIG. 1, and/or the computer device 500 of FIG. 5.

At block 402, the process may receive an image of a surface captured by a camera, wherein the surface is illuminated by a light source positioned at an angle to the surface. In embodiments, the surface may be a substrate surface that includes surface 106 with bumps 108 or material 110 of FIG. 1. In embodiments, the surface may be any surface. In embodiments, the light source 104 may be positioned at an angle, for example, between 15° and 45°, relative to a plane of the surface. In embodiments, the light source 104 may be positioned in substantially the same location and direction as the camera 102. In other embodiments, the light source 104 may be positioned in any suitable direction where light may be reflected off the surface 106 and away from the camera 102 (such as light rays 104*c* of FIG. 1) as if the surface 106 were a mirror. In embodiments, the light source 104 may be a light bar, and may produce collimated or substantially collimated light.

At block 404, the process may analyze the received image to identify a measurement of light intensity of one or more portions of the surface. In embodiments, the captured image of the surface may be similar to diagram 200 of FIG. 2, or of diagrams 300*a*, 300*b* of FIG. 3. In embodiments, based upon the position of the camera, such as camera 102 of FIG. 1 where the camera 102 is not directly above the surface 106, the resulting image of the surface 106 may have perspective distortion. For example, an image of a rectangular shaped surface may appear as a trapezoidal surface, with an edge of the surface nearest the camera 102 that may appear shorter than an edge of the surface farthest from the camera 102. In these embodiments, the image perspective may be corrected prior to further analysis by using mathematical formulas based upon the position of the camera 102 relative to the surface 106 and/or optical properties of the camera 102. In embodiments, this perspective correction may result in an image that may appear as a nadir image captured by a camera 102 directly above the surface 106 with a lens pointing perpendicular to the surface 106. Image perspective correction may also ensure that the comparative sizes of regions on the surface 106 areas may be measured in consistent units.

In embodiments, it may be desirable to analyze only specific areas within an image, for example, only areas 330, 332, 334 of image 300*b*. In these embodiments, a segmentation process may be used to isolate or otherwise identify specific regions within the image to which the analysis should be applied. In embodiments, the segmentation process may use color difference, edge detection, pre-identified image coordinates, or some other appropriate segmentation technique.

In embodiments, regions within the image to which analysis should be applied may further be subjected to a normalization process. In embodiments, this normalization process may include converting a region within the image to a grayscale. The normalization process may also include smoothing the image, for example, using a Gaussian filter to reduce image noise. The normalization process may enhance image contrast between presence and absence of the applied materials in preparation for image analysis.

In embodiments, image analysis may then be applied to perspective corrected and normalized regions of the surface to identify lighter or darker regions of the surface that may indicate the absence or presence of material, such as material 110 on surface 106. In embodiments, a determined threshold intensity value may be used to identify regions of the surface having flux or not having flux.

In embodiments, an intensity ratio may be determined as the ratio between an average intensity of a region of a surface and a reference point of a textured surface. An intensity ratio may be determined for areas on a surface that may or may not have a material such as flux covering the surface. In embodiments, a first region of the surface without flux may have a higher intensity ratio than a second region with flux. In embodiments, a substrate area proximate to a bump area may be used as a local reference point of a textured surface. This may enhance the analysis process by reducing the effect of light illumination intensity variation over the field of view.

At block 406, the process may determine, based on the analysis, whether each of the one or more portions of the surface includes a threshold amount of a material on the surface. In embodiments, a threshold amount of material, or a lack of a threshold amount of material, may be identified as one or more boundary areas, such as boundary area 336a on image 336, boundary areas 338a, 338b on image 338, or boundary areas 340a, 340b, 340c on image 340, having insufficient material on the surface.

Figure 5:
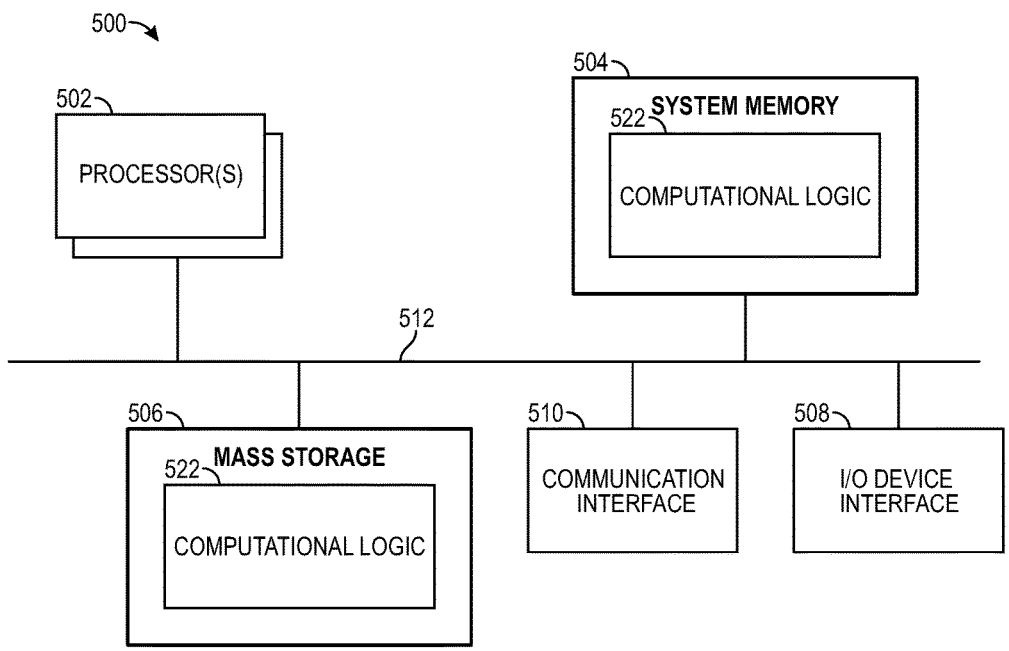
FIG. 5 illustrates an example computer system, suitable for use to practice the present disclosure (or aspects thereof), in accordance with various embodiments.

FIG. 5 illustrates an example computer system, suitable for use to practice the present disclosure (or aspects thereof), in accordance with various embodiments. As shown, in embodiments, computer device 500 may include one or more processors 502 and system memory 504. Each processor 502 may include one or more processor cores. In embodiments, the processors 502 may execute a plurality of threads, wherein one or more neurons of a layer of a multi-layer neural network may operate in one of the plurality of execution threads. System memory 504 may include any known volatile or non-volatile memory. Additionally, computer device 500 may include mass storage device(s) 506 (such as solid-state drives), input/output (I/O) device interface 508 (to interface with, e.g., camera 102, light source 104, sensors, etc.) and communication interfaces 510 (such as serial interface, near field communication, network interface cards, modems and so forth). The elements may be coupled to each other via system bus 512, which may represent one or more buses. In the case of multiple buses, they may be bridged by one or more bus bridges (not shown).

Each of these elements may perform its conventional functions known in the art. In particular, system memory 504 and mass storage device(s) 506 may be employed to store a working copy and a permanent copy of the executable code of the programming instructions in computational logic 522 implementing the operations described earlier. These operations may include, but are not limited to operations associated with the light source 104 or camera 102 of FIG. 1, or of the inspection module that may include operations as described in FIGS. 1-4. The programming instructions may comprise assembler instructions supported by processor(s) 502 or high-level languages, such as, for example, C, that can be compiled into such instructions.

The permanent copy of the executable code of the programming instructions and/or the bit streams to configure a hardware accelerator (not shown) may be placed into permanent mass storage device(s) 506 or the hardware accelerator (not shown) in the factory, or in the field, through, for example, a distribution medium (not shown), such as a compact disc (CD), or through communication interface 510 (from a distribution server (not shown)).

Figure 6:
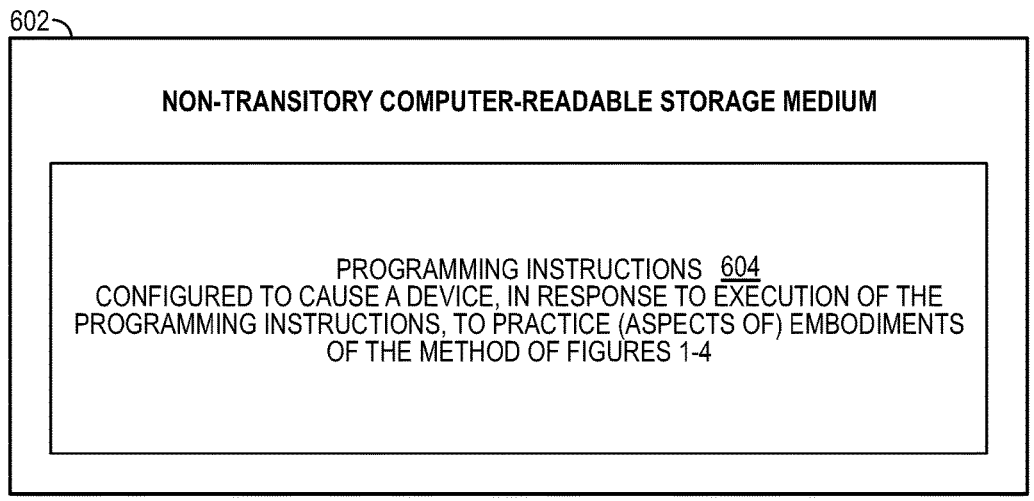
FIG. 6 illustrates an example storage medium with instructions configured to enable a computer system to practice the present disclosure, in accordance with various embodiments.

FIG. 6 illustrates an example storage medium with instructions configured to enable a computer system to practice the present disclosure, in accordance with various embodiments.

As illustrated, non-transitory computer-readable storage medium 602 may include the executable code of a number of programming instructions 604. Executable code of programming instructions 604 may be configured to enable a system, e.g., computer device 500 of FIG. 5, in response to execution of the executable code/programming instructions, to perform, e.g., various operations associated with higher order multilayer neural networks using homogeneous symmetric tensors. In alternate embodiments, executable code/programming instructions 604 may be disposed on multiple non-transitory computer-readable storage media 602 instead. In still other embodiments, executable code/programming instructions 604 may be encoded in transitory computer-readable media, such as signals.

In embodiments, a processor may be packaged together with a computer-readable storage medium having some, or all of executable code 604 based on programming instructions configured to practice all or selected ones of the operations earlier described. For one embodiment, a processor may be packaged together with such executable code 604 to form a System in Package (SiP). For one embodiment, a processor may be integrated on the same die with a computer-readable storage medium having such executable code 604. For one embodiment, a processor may be packaged together with a computer-readable storage medium having such executable code 604 to form a System on Chip (SoC).

EXAMPLES

Example 1 may be an apparatus comprising: one or more processors; an inspection module communicatively coupled to the one or more processors to: receive an image of a surface captured by a camera, wherein the surface is illuminated by a light source positioned at an angle to the surface; analyze the received image to identify a measurement of light intensity of one or more portions of the surface; and determine, based on the analysis, whether each of the one or more portions of the surface includes a threshold amount of a material on the surface.

Example 2 may include the apparatus of example 1, or of any other example described herein, wherein the light source is at an angle between 15° and 45° relative to a plane of the surface.

Example 3 may include the apparatus of example 1, or any other example described herein, wherein the light source produces collimated light.

Example 4 may include the apparatus of example 1, or of any other example described herein, wherein the camera and the light source are located substantially adjacent to each other.

Example 5 may include the apparatus of example 1, or of any other example described herein, wherein the camera is substantially orthogonal to the plane of the surface.

Example 6 may include the apparatus of example 1, or of any other example described herein, wherein the camera has a depth of field such that the each of the one or more portions of the surface is substantially in focus.

Example 7 may include the apparatus of example 1, or of any other example described herein, wherein the inspection module is further to convert the received image to a nadir image of the surface.

Example 8 may include the apparatus of example 7, or of any other example described herein, wherein the inspection module is further to blur the nadir image of the surface.

Example 9 may include the apparatus of example 1, or of any other example described herein, wherein the inspection module is further to: determine, based on the analysis, a ratio of coverage of the material on the surface; and output an indication of the determined ratio of coverage.

Example 10 may include the apparatus of example 9, or of any other example described herein, wherein the ratio of coverage is a percentage.

Example 11 may include the apparatus of example 1, or of any other example described herein, wherein to analyze the received image further includes to: identify a first average light intensity for a portion of the surface without the material on the surface; identify a second average light intensity for each of the one or more portions of the surface; and compare the first average light intensity with each of the second average light intensity for the each of the one or more portions of the surface.

Example 12 may include the apparatus of example 1, or of any other example described herein, wherein the threshold amount of material on the surface is a thickness of the material on the surface.

Example 13 may include the apparatus of example 1, or of any other example described herein, wherein the material is a selected one of: a flux, solder paste, epoxy, or transparent coating.

Example 14 may include the apparatus of example 1, or of any other example described herein, wherein the material on the surface is to cause a smoothing of the surface.

Example 15 may include the apparatus of example 1, or of any other example described herein, further comprising based on the determination, output an indication of whether the each of the one or more portions of the surface includes the threshold amount of the material.

Example 16 may include the apparatus of claim 1, or of any other example described herein, wherein the apparatus includes the light source.

Example 17 may include the apparatus of example 1, or of any other example described herein, wherein the apparatus includes the camera.

Example 18 may be a method comprising: receiving an image of a surface captured by a camera, wherein the surface is illuminated by a light source positioned at an angle to the surface; analyzing the received image to identify a measurement of light intensity of one or more portions of the surface; and determining, based on the analysis, whether each of the one or more portions of the surface includes a threshold amount of a material on the surface.

Example 19 may include the method of example 18, or of any other example described herein, wherein the light source is at an angle between 15° and 45° relative to a plane of the surface.

Example 20 may include the method of example 18, or any other example described herein, wherein the light source produces collimated light.

Example 21 may include the method of example 18, or of any other example described herein, wherein the camera and the light source are located substantially adjacent to each other.

Example 22 may include the method of example 18, or of any other example described herein, wherein the camera is substantially orthogonal to the plane of the surface.

Example 23 may include the method of example 18, or of any other example described herein, wherein the camera has a depth of field such that the each of the one or more portions of the surface is substantially in focus.

Example 24 may include the method of example 18, or of any other example described herein, further comprising converting the received image to a nadir image of the surface.

Example 25 may include the method of example 24, or of any other example described herein, further comprising blurring the nadir image of the surface.

Example 26 may include the method of example 18, or of any other example described herein, further comprising: determining, based on the analysis, a ratio of coverage of the material on the surface; and outputting an indication of the determined ratio of coverage.

Example 27 may include the method of example 26, or of any other example described herein, wherein the ratio of coverage is a percentage.

Example 28 may include the method of example 18, or of any other example described herein, wherein analyzing the received image further includes: identifying a first average light intensity for a portion of the surface without the material on the surface; identifying a second average light intensity for each of the one or more portions of the surface; and comparing the first average light intensity with each of the second average light intensity for the each of the one or more portions of the surface.

Example 29 may include the method of example 18, or of any other example described herein, wherein the threshold amount of material on the surface is a thickness of the material on the surface.

Example 30 may include the method of example 18, or of any other example described herein, wherein the material is a selected one of: a flux, solder paste, epoxy, or transparent coating.

Example 31 may include the method of example 18, or of any other example described herein, wherein the material on the surface is to cause a smoothing of the surface.

Example 32 may include the method of example 18, or of any other example described herein, further comprising, based on the determination, outputting an indication of whether the each of the one or more portions of the surface includes the threshold amount of the material.

Example 33 may be one or more computer-readable media comprising instructions that cause a computing device, in response to execution of the instructions by the computing device, to: receive an image of a surface captured by a camera, wherein the surface is illuminated by a light source positioned at an angle to the surface; analyze the received image to identify a measurement of light intensity of one or more portions of the surface; and determine, based on the analysis, whether each of the one or more portions of the surface includes a threshold amount of a material on the surface.

Example 34 may include the computer-readable media of example 33, or of any other example described herein, wherein the light source is at an angle between 15° and 45° relative to a plane of the surface.

Example 35 may include the computer-readable media of example 33, or of any other example described herein, wherein the light source produces collimated light.

Example 36 may include the computer-readable media of example 33, or of any other example described herein, wherein the camera and the light source are located substantially adjacent to each other.

Example 37 may include the computer-readable media of example 33, or of any other example described herein, wherein the camera is substantially orthogonal to the plane of the surface.

Example 38 may include the computer-readable media of example 33, or of any other example described herein, wherein the camera has a depth of field such that the each of the one or more portions of the surface is substantially in focus.

Example 39 may include the computer-readable media of example 33, or of any other example described herein, further comprising converting the received image to a nadir image of the surface.

Example 40 the computer-readable media of example 39, or of any other example described herein, further comprising blurring the nadir image of the surface.

Example 41 may include the computer-readable media of example 33, or of any other example described herein, further to: determine, based on the analysis, a ratio of coverage of the material on the surface; and output an indication of the determined ratio of coverage.

Example 42 may include the computer-readable media of example 41, or of any other example described herein, wherein the ratio of coverage is a percentage.

Example 43 may include the computer-readable media of example 33, or of any other example described herein, wherein to analyze the received image further includes to: identify a first average light intensity for a portion of the surface without the material on the surface; identify a second average light intensity for each of the one or more portions of the surface; and compare the first average light intensity with each of the second average light intensity for the each of the one or more portions of the surface.

Example 44 may include the computer-readable media of example 33, or of any other example described herein, wherein the threshold amount of material on the surface is a thickness of the material on the surface.

Example 45 may include the computer-readable media of example 33, or of any other example described herein, wherein the material is a selected one of: a flux, solder paste, epoxy, or transparent coating.

Example 46 may include the computer-readable media of example 33, or of any other example described herein, wherein the material on the surface is to cause a smoothing of the surface.

Example 47 may include the computer-readable media of example 33, or of any other example described herein, further to output, based on the determination, an indication of whether the each of the one or more portions of the surface includes the threshold amount of the material.

Example 48 may be an apparatus comprising: means for receiving an image of a surface captured by a camera, wherein the surface is illuminated by a light source positioned at an angle to the surface; means for analyzing the received image to identify a measurement of light intensity of one or more portions of the surface; and means for determining, based on the analysis, whether each of the one or more portions of the surface includes a threshold amount of a material on the surface.

Example 49 may include the apparatus of example 48, or of any other example described herein, wherein the light source is at an angle between 15° and 45° relative to a plane of the surface.

Example 50 may include the apparatus of example 48, or of any other example described herein, wherein the light source produces collimated light.

Example 51 may include the apparatus of example 48, or of any other example described herein, wherein the camera and the light source are located substantially adjacent to each other.

Example 52 may include the apparatus of example 48, or of any other example described herein, wherein the camera is substantially orthogonal to the plane of the surface.

Example 53 may include the apparatus of example 48, or of any other example described herein, wherein the camera has a depth of field such that the each of the one or more portions of the surface is substantially in focus.

Example 54 may include the apparatus of example 48, or of any other example described herein, further comprising converting the received image to a nadir image of the surface.

Example 55 may include the apparatus of example 54, or of any other example described herein, further comprising blurring the nadir image of the surface.

Example 56 may include the apparatus of example 48, or of any other example described herein, further comprising: means for determining, based on the analysis, a ratio of coverage of the material on the surface; and means for outputting an indication of the determined ratio of coverage.

Example 57 may include the apparatus of example 56, or of any other example described herein, wherein the ratio of coverage is a percentage.

Example 58 may include the apparatus of example 48, or of any other example described herein, wherein analyzing the received image further includes: means for identifying a first average light intensity for a portion of the surface without the material on the surface; means for identifying a second average light intensity for each of the one or more portions of the surface; and means for comparing the first average light intensity with each of the second average light intensity for the each of the one or more portions of the surface.

Example 59 may include the apparatus of example 48, or of any other example described herein, wherein the threshold amount of material on the surface is a thickness of the material on the surface.

Example 60 may include the apparatus of example 48, or of any other example described herein, wherein the material is a selected one of: a flux, solder paste, epoxy, or transparent coating.

Example 61 may include the apparatus of example 48, or of any other example described herein, wherein the material on the surface is to cause a smoothing of the surface.

Example 62 may include the apparatus of example 48, or of any other example described herein, further comprising, based on the determination, means for outputting an indication of whether the each of the one or more portions of the surface includes the threshold amount of the material.

Example 63 may be a system comprising: one or more processor; an inspection module communicatively coupled to the one or more processors to: receive an image of a surface captured by a camera, wherein the surface is illuminated by a light source positioned at an angle to the surface; analyze the received image to identify a measurement of light intensity of one or more portions of the surface; and determine, based on the analysis, whether each of the one or more portions of the surface includes a threshold amount of a material on the surface, and the camera communicatively coupled to the one or more processors.

Example 64 may include the system of example 63, or of any other example described herein, wherein the light source is at an angle between 15° and 45° relative to a plane of the surface.

Example 65 may include the system of example 63, or of any other example described herein, wherein the light source produces collimated light.

Example 66 may include the system of example 63, or of any other example described herein, wherein the camera and the light source are located substantially adjacent to each other.

Example 67 may include the system of example 63, or of any other example described herein, wherein the camera is substantially orthogonal to the plane of the surface.

Example 68 may include the system of example 63, or of any other example described herein, wherein the camera has a depth of field such that the each of the one or more portions of the surface is substantially in focus.

Example 69 may include the system of example 63, or of any other example described herein, wherein the inspection module is further to convert the received image to a nadir image of the surface.

Example 70 may include the system of example 69, or of any other example described herein, wherein the inspection module is further to blur the nadir image of the surface.

Example 71 may include the system of example 63, or of any other example described herein, wherein the inspection module is further to: determine, based on the analysis, a ratio of coverage of the material on the surface, and output an indication of the determined ratio of coverage.

Example 72 may include the system of example 71, or of any other example described herein, wherein the ratio of coverage is a percentage.

Example 73 may include the system of example 63, or of any other example described herein, wherein to analyze the received image further includes to: identify a first average light intensity for a portion of the surface without the material on the surface, identify a second average light intensity for each of the one or more portions of the surface, and compare the first average light intensity with each of the second average light intensity for the each of the one or more portions of the surface.

Example 74 may include the system of example 63, or of any other example described herein, wherein the threshold amount of material on the surface is a thickness of the material on the surface.

Example 75 may include the system of example 63, or of any other example described herein, wherein the material is a selected one of: a flux, solder paste, epoxy, or transparent coating.

Example 76 may include the system of example 63, or of any other example described herein, wherein the material on the surface is to cause a smoothing of the surface.

Example 77 may include the system of example 63, or of any other example described herein, further comprising based on the determination, output an indication of whether the each of the one or more portions of the surface includes the threshold amount of the material.

Example 78 may include the system of example 63, or of any other example described herein, wherein the apparatus includes the light source.

Example 79 may include an apparatus comprising means to perform one or more elements of a method described in or related to any of examples 1-78, or any other example described herein.

Example 80 may include one or more non-transitory computer-readable media comprising instructions to cause an electronic device, upon execution of the instructions by one or more processors of the electronic device, to perform one or more elements of a method described in or related to any of examples 1-78, or any other example described herein.

Example 81 may include an apparatus comprising logic, modules, or circuitry to perform one or more elements of a method described in or related to any of examples 1-78, or any other example described herein.

Example 82 may include a method, technique, or process as described in or related to any of examples 1-78, or portions or parts thereof.

Example 83 may include an apparatus comprising: one or more processors and one or more computer readable media comprising instructions that, when executed by the one or more processors, cause the one or more processors to perform the method, techniques, or process as described in or related to any of examples 1-78, or portions thereof.

Various embodiments may include any suitable combination of the above-described embodiments including alternative (or) embodiments of embodiments that are described in conjunctive form (and) above (e.g., the "and" may be "and/or"). Furthermore, some embodiments may include one or more articles of manufacture (e.g., non-transitory computer-readable media) having instructions, stored thereon, that when executed result in actions of any of the above-described embodiments. Moreover, some embodiments may include apparatuses or systems having any suitable means for carrying out the various operations of the above-described embodiments.

The above description of illustrated embodiments, including what is described in the Abstract, is not intended to be exhaustive or to limit embodiments to the precise forms disclosed. While specific embodiments are described herein for illustrative purposes, various equivalent modifications are possible within the scope of the embodiments, as those skilled in the relevant art will recognize.

These modifications may be made to the embodiments in light of the above detailed description. The terms used in the following claims should not be construed to limit the embodiments to the specific implementations disclosed in the specification and the claims. Rather, the scope of the invention is to be determined entirely by the following claims, which are to be construed in accordance with established doctrines of claim interpretation.

What is claimed is:

1. An apparatus comprising:
one or more processors;
an inspection module communicatively coupled to the one or more processors to:
  receive an image of a surface captured by a camera, wherein the surface is illuminated by a light source positioned at an angle to the surface;
  analyze the received image to identify a measurement of light intensity of one or more portions of the surface; and
  determine, based on the analysis, whether each of the one or more portions of the surface includes a threshold amount of a material on the surface.

2. The apparatus of claim 1, wherein the light source is at an angle between 15° and 45° relative to a plane of the surface.

3. The apparatus of claim 1, wherein the light source produces collimated light.

4. The apparatus of claim 1, wherein the camera and the light source are located substantially adjacent to each other.

5. The apparatus of claim 1, wherein the camera is substantially orthogonal to a plane of the surface.

6. The apparatus of claim 1, wherein the camera has a depth of field such that the each of the one or more portions of the surface is substantially in focus.

7. The apparatus of claim 1, wherein the inspection module is further to convert the received image to a nadir image of the surface.

8. The apparatus of claim 7, wherein the inspection module is further to blur the nadir image of the surface.

9. The apparatus of claim 1, wherein the inspection module is further to:
determine, based on the analysis, a ratio of coverage of the material on the surface; and
output an indication of the determined ratio of coverage.

10. The apparatus of claim 1, wherein to analyze the received image further includes to:
  identify a first average light intensity for a portion of the surface without the material on the surface;
  identify a second average light intensity for each of the one or more portions of the surface; and
  compare the first average light intensity with each of the second average light intensity for the each of the one or more portions of the surface.

11. The apparatus of claim 1, wherein the material is a selected one of: a flux, solder paste, epoxy, or transparent coating.

12. The apparatus of claim 1, wherein the material on the surface is to cause a smoothing of the surface.

13. The apparatus of claim 1, further comprising based on the determination, output an indication of whether the each of the one or more portions of the surface includes the threshold amount of the material.

14. A method comprising:
  receiving an image of a surface captured by a camera, wherein the surface is illuminated by a light source positioned at an angle to the surface;
  analyzing the received image to identify a measurement of light intensity of one or more portions of the surface; and
  determining, based on the analysis, whether each of the one or more portions of the surface includes a threshold amount of a material on the surface.

15. The method of claim 14, wherein the camera and the light source are located substantially adjacent to each other.

16. The method of claim 14, wherein the camera is substantially orthogonal to a plane of the surface.

17. The method of claim 14, further comprising:
  determining, based on the analysis, a ratio of coverage of the material on the surface; and
  outputting an indication of the determined ratio of coverage.

18. One or more computer-readable media comprising instructions that cause a computing device, in response to execution of the instructions by the computing device, to:
  receive an image of a surface captured by a camera, wherein the surface is illuminated by a light source positioned at an angle to the surface;
  analyze the received image to identify a measurement of light intensity of one or more portions of the surface; and
  determine, based on the analysis, whether each of the one or more portions of the surface includes a threshold amount of a material on the surface.

19. The computer-readable media of claim 18, further comprising converting the received image to a nadir image of the surface.

20. The computer-readable media of claim 18, further to:
  determine, based on the analysis, a ratio of coverage of the material on the surface; and
  output an indication of the determined ratio of coverage.

21. The computer-readable media of claim 18, wherein to analyze the received image further includes to:
  identify a first average light intensity for a portion of the surface without the material on the surface;
  identify a second average light intensity for each of the one or more portions of the surface; and
  compare the first average light intensity with each of the second average light intensity for the each of the one or more portions of the surface.

22. The computer-readable media of claim 18, further to output, based on the determination, an indication of whether the each of the one or more portions of the surface includes the threshold amount of the material.

23. An system comprising:
  one or more processors;
  an inspection module communicatively coupled to the one or more processors to:
    receive an image of a surface captured by a camera, wherein the surface is illuminated by a light source positioned at an angle to the surface;
    analyze the received image to identify a measurement of light intensity of one or more portions of the surface; and
    determine, based on the analysis, whether each of the one or more portions of the surface includes a threshold amount of a material on the surface; and
  the camera communicatively coupled to the one or more processors.

24. The system of claim 23, wherein the light source is at an angle between 15° and 45° relative to a plane of the surface.

25. The system of claim 23, wherein the inspection module is further to:
  determine, based on the analysis, a ratio of coverage of the material on the surface; and
  output an indication of the determined ratio of coverage.

* * * * *